United States Patent [19]

Murray et al.

[11] Patent Number: 4,898,952
[45] Date of Patent: Feb. 6, 1990

[54] REGIOSELECTIVE SYNTHESIS OF A 1,5-DISUBSTITUTED PYRAZOLE

[75] Inventors: William V. Murray, Belle Mead; Michael P. Wachter, Bloomsbury, both of N.J.

[73] Assignee: Ortho Pharmaceutical Corporation, Raritan, N.J.

[21] Appl. No.: 307,140

[22] Filed: Feb. 6, 1989

Related U.S. Application Data

[63] Continuation of Ser. No. 55,807, May 29, 1987, abandoned.

[51] Int. Cl.$^4$ .............................................. C07D 231/12
[52] U.S. Cl. ..................................... 548/378; 562/459
[58] Field of Search ......................................... 548/378

[56] References Cited

U.S. PATENT DOCUMENTS

| | | | |
|---|---|---|---|
| 3,899,508 | 8/1975 | Wikel | 548/378 |
| 4,095,025 | 6/1978 | Newberry | 548/378 |
| 4,826,868 | 5/1989 | Wachter et al. | 514/407 |

*Primary Examiner*—Robert W. Ramsuer

[57] ABSTRACT

A highly regioselective synthesis of pyrazoles from a mono-substituted hydrazine and a β-dicarbonyl compound wherein a carboxylic acid moiety is present on the substituent attached to one of the carbonyls. For example, compounds of the formula (I) are formed in marked preference to isomers of formula (IV):

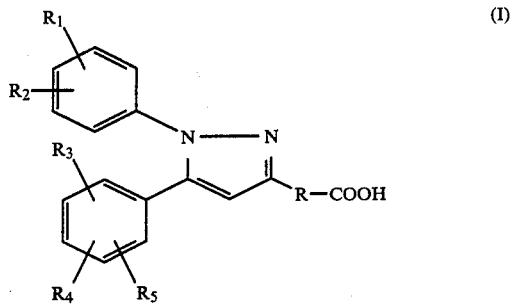

(I)

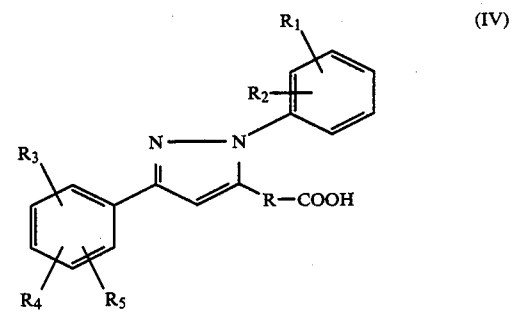

(IV)

1 Claim, No Drawings

REGIOSELECTIVE SYNTHESIS OF A 1,5-DISUBSTITUTED PYRAZOLE

This is a continuation of U.S. Ser. No. 55,807 filed May 29, 1987 now abandoned.

BACKGROUND OF THE INVENTION

The standard synthesis for pyrazoles involves the reaction of a β-dicarbonyl compound with a hydrazine under mild conditions, see A. R. Katritzky in "The Principles of Heterocyclic Chemistry", Academic Press, New York (1968) at page 139. However, when the hydrazine is mono-substituted and the substituents attached to the two carbonyls of the β-dicarbonyl compound are not the same, two isomer products are possible. Thus, preparations of the anti-inflammatory compounds (I) may involve co-synthesis of significant percentages of the isomer of formula (IV):

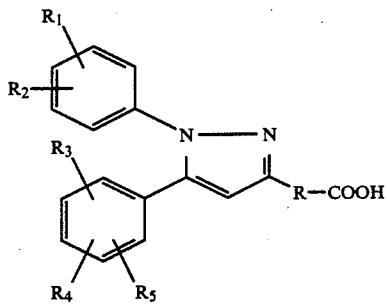

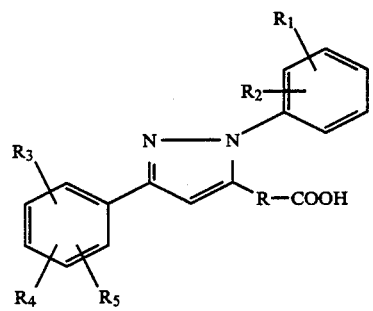

While the 1,5-diphenyl pyrazoles of formula (I) have excellent activity in alleviating inflammation and inhibit the cyclooxygenase and/or lipoxygenase pathways, the 1,3-diphenylpyrazoles do not show such excellent activity. Therefore, it would be advantageous to provide a synthesis of pyrazoles which minimizes or eliminated production of the undesirable isomer.

SUMMARY OF THE INVENTION

It has been found that a high degree of regioselectivity can be achieved in the synthesis of pyrazoles from a mono-substituted hydrazine by providing a carboxylic acid moiety indirectly on one of the carbonyls of the β-dicarbonyl compound used in the synthesis.

DETAILED DESCRIPTION OF THE INVENTION

In a first embodiment of the process of the invention, a 1,5-diphenyl pyrazole of the following formula (I)

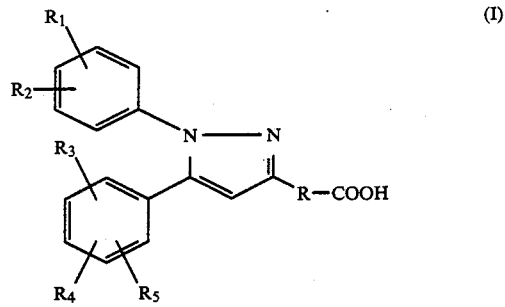

wherein
$R_1$, $R_2$, $R_3$, $R_4$ and $R_5$ are the same or different and are individually selected from the group consisting of hydrogen, lower alkyl, lower alkoxy, phenyl, halo, hydroxy, lower alkylsulfonyl, lower alkylthio, nitro, trifluoromethyl, omega-trifluoromethyl lower alkoxy, amino, acetamino or $R_1R_2$ or $R_3R_4R_5$, taken together with the phenyl group to which they are attached, form a naphthyl or substituted naphthyl group; and R is a straight chained, saturated or unsaturated hydrocarbon that contains 2–12 carbon atoms;
with the provisos that:
at least one of $R_1$ and $R_2$ is other than hydrogen where (i) R is $(CH_2)_2$ and (ii) $R_3$, $R_4$ and $R_5$ are 4-methoxy, H and H; 3-methoxy, 4-hydroxy and H; 2-hydroxy, H and H; or all of $R_3$, $R_4$ and $R_5$ are hydrogen and
at least one of $R_1$ and $R_2$, or of $R_3$, $R_4$ and $R_5$ is other than hydrogen where the RCOOH moiety contains three saturated carbon atoms linked together by carbon-carbon bonds;

and pharmaceutically acceptable salts thereof is prepared by a process which comprises reacting a hydrazine of the following formula (II) with a dione acid of the following formula (III):

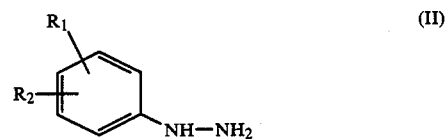

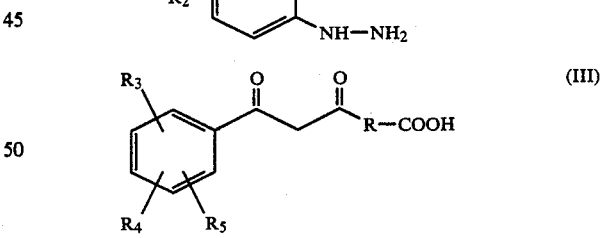

Compounds of the formula (I) are useful as anti-inflammatory agents in mammals or may be used as intermediates to prepare compounds of formula (I) wherein (i) the hydrogen at the 4-position is replaced by bromo, chloro or lower alkyl, and/or (ii) where the —COOH group is replaced by a variety of moieties, e.g. —CON(CH$_3$)OH, by refunctionalization reactions as known in the art. The pharmaceutical activity and compositions of compounds of formula (I) as well as derivatives according to said changes (i) and/or (ii) are described in copending U.S. Ser. Nos. 867,996 filed May 29, 1986 now abandoned and 42,661 filed Apr. 29, 1987 now U.S. Pat. No. 4,826,868 which are incorporated by reference. In more detail, in the above formula (I), $R_1$, $R_2$, $R_3$, $R_4$ and $R_5$ are substituents on phenyl rings that substitute for hydrogen atoms at positions 1 and 5 of the pyrazole ring. It is preferred that at least one of $R_1$ and $R_2$, and one of $R_3$, $R_4$ and $R_5$ be substituted at the 4-positions of their respective phenyl rings. In the above structural formula to which the useful pyrazole compounds conform, it is noted that the $R_1$, $R_2$, $R_3$, $R_4$ and $R_5$ radicals can be a "lower" alkyl, "lower" alkoxy and the like. Groups and radicals referred to as "lower" denote that they possess 1 to about 6 carbon atoms. The same is true for "lower" groups and radicals that are substituents of the "lower" groups and radicals enumerated. Lower alkyl radicals include, for example, methyl, ethyl, propyl, isopropyl, n-butyl, sec-butyl, t-butyl, n-pentyl, 2-methyl-3-butyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, octyl and the like. Lower alkoxy radicals are oxygen ethers formed from a before-described lower alkyl group. Exemplary radicals include methoxy, ethoxy, propoxy, isopropoxy, n-butoxy, and the like. Lower alkylthio radicals of $R_1$, $R_2$, $R_3$ and $R_4$ are sulfide ethers and are thus analogous to the oxygen ethers described above. Halo radicals preferably include chloro and bromo, as well as fluoro and iodo. Lower alkylsulfonyl radicals contain a before-described lower alkyl radical bonded to an $SO_2$ moiety that is itself also bonded to a phenyl ring. Exemplary lower alkylsulfonyl radicals thus include methylsulfonyl, ethylsulfonyl, 2-ethylbutylsulfonyl and the like. An omega-trifluoromethyl lower alkoxy radical is a lower alkoxy radical as before described that additionally includes a trifluoromethyl group at a position farthest on the alkyl chain from the place of bonding to the phenyl ring. Exemplary of such radicals are the 2,2,2-trifluoroethoxy. Naphthyl and substituted naphthyl radicals can replace an aryl group herein at either the 1- or 2-positions to provide 1-naphthyl or 2-naphthyl substituents, respectfully. Substituents on the naphthyl radicals can be any of those described herein as being useful aryl substituents. Exemplary substituted 1- and 2-naphthyls include 6-methoxy-2-naphthyl and the like.

R in the structural formulae above is a straight, saturated or unsaturated hydrocarbyl radical that contains 2 to about 12 carbon atoms. In particular, the R—COOH radical together contains three saturated carbon atoms linked together by carbon-carbon bonds. In other preferred embodiments, R is unsaturated and contains 2-5 carbon atoms. R is a hydrocarbon radical and therefore contains no elements other than carbon and hydrogen. In a particular embodiment, $R_1$ is hydrogen; $R_2$ is methoxy at the 4-position; $R_3$ is 4-methyl, 3-methyl, 4-chloro, 2-methyl or 3-ethyl and $R_4$ and $R_5$ are hydrogen, or $R_3$ is 3-methyl, $R_4$ is 4-methyl and $R_5$ is hydrogen, or $R_3$ is 2-methyl, $R_4$ is 4-methyl and $R_5$ is 6methyl; and R is —$CH_2CH_2$—.

In particular, $R_2$, $R_4$ and $R_5$ in formula (I) are hydrogen, and $R_1$ and $R_3$ are selected from the group consisting of halo, $CH_3$, lower alkyl and lower alkoxy, e.g. halo and lower alkoxy, especially methoxy. The preferred $R_1$ and $R_3$ substituents are preferably at the 4-positions of their respective aryl (phenyl) rings. It is preferred that R contain two carbon atoms.

A pharmaceutical composition that comprises an anti-inflammatory amount of a 1,5-diaryl-3-substituted pyrazole compound of formula (I) dispersed in a pharmaceutically acceptable carrier. The compounds of formula (I) are capable of inhibiting the lipoxygenase enzyme pathway and/or the cyclooxygenase (prostaglandin synthetase) enzyme pathway. The amount of active ingredient that is administered in vivo depends on the age and weight of the mammal treated, the particular medical condition to be treated, the frequency of administration, and the route of administration. The dose range can be about 0.01 to about 500 milligrams per kilogram of body weight, more preferably about 0.1 to about 50 milligrams per kilogram of body weight and most preferably about 0.1 to about 25 milligrams per kilogram of body weight. The human adult dose is in the range of about 10 to about 2000 milligrams daily, given as a single dose or in 3 or 4 divided doses. Veterinary dosages correspond to human dosages with the amounts administered being in proportion to the weight of the animal as compared to adult humans. Orally administered unit doses containing about 1 to about 50 milligrams of a 1,5-diaryl-3-substituted pyrazole of formula (I) per kilogram of laboratory rat body weight (e.g., about 200 grams each) were useful in reducing inflammation. These results are contrary to those reported by Virmani et al., *Indian J. Chem., Sect. B* 17: 472-477 (1979) who reported compounds that are structurally similar to those described herein were not active as anti-inflammatory agents. Physiologically tolerable carriers are well known in the art. Exemplary of liquid carriers are aqueous solutions that contain no materials in addition to the substituted pyrazole compound, or contain a buffer such as sodium phosphate at physiological pH value, saline and the like. Liquid compositions can also contain liquid phases in addition to and to the exclusion of water. Exemplary of such additional liquid phases are glycerin and vegetable oils such as cottonseed oil. Exemplary solid carriers (diluents) include those materials usually used in the manufacture of pills or tablets, and include corn starch, lactose, dicalcium phosphate, thickeners such as tragacanth and methylcellulose U.S.P., finely divided $SiO_2$, polyvinylpyrrolidone, magnesium stearate and the like. Antioxidants such as methylparaben and propylparaben can be present in both solid and liquid compositions, as can sweeteners such as cane or beet sugar, sodium saccharin, sodium cyclamate and the dipeptide methyl ester sweetener sold under the trademark NUTRASWEET (aspartame) by G. D. Searle Co. The pharmaceutical composition can be administered orally, topically or by injection, by means well known in the art. In preferred practice, the composition is administered orally as a tablet, capsule or aqueous dispersion. Inasmuch as a pharmaceutical composition can be administered 3 to 4 times daily (per 24 hour period), the method of alleviating inflammation can include administering the pharmaceutical composition a plurality of times into the treated mammal over a time period of weeks, months and years. The pharmaceutical composition is administered a plurality of times to the mammal over a time period of thirty days, in preferred practice.

In the process of the first embodiment, the reaction between the compounds of formulae (II) and (III) is conducted at a molar ratio of about 1:1 and at a temperature of about 0° to 100° C., e.g. about 65° to 80° C. This can be accomplished by refluxing for about 1 to 24 hours in an inert solvent such as an alcohol such as methanol. The product of formula (I) may be recovered by crystallization of chromatography. When used as an intermediate, the COOH of the compound of formula (I) may be transformed into those of formula (I) where, however, the —COOH is refunctionalized through techniques known in the art, to a group of the formula C(O)—R' wherein R' is selected from the group consisting of hydrogen, alkyl, lower alkoxy, NR$_6$R$_7$ wherein R$_6$ and R$_7$ are the same or different and are selected from the group consisting of hydrogen and lower alkyl, or R$_6$ or R$_7$ are selected from the group consisting of hydrogen, lower alkyl, lower alkoxy, hydroxy, acyloxy, benzyloxy, 2-hydroxy lower alkyl, lower alkyl carboxy, phenyl, substituted phenyl, pyridyl, thiazolyl, dihydrothiazolyl, 5-tetrazolyl, —OCO(CH$_2$)$_n$COR$_9$ wherein R$_9$ is —OH, —ONa, dialkylamino such as diethylamino and morpholino, and n is 2 or 3, R$_6$ and R$_7$ also possibly being —OCOR$_{10}$ wherein R$_{10}$ is —CH$_2$NR$_{11}$R$_{12}$ wherein R$_{11}$ and R$_{12}$ are independently hydrogen, alkyl, such as methyl, cycloalkyl such as cyclohexyl, or together are a heterocyclic ring such as N-methylpiperazino, —OCOR$_{10}$ can also be defined as wherein R$_{10}$ is —CH$_2$Cl, —CH$_2$O—loweralkyl, t-butyl, —CH—loweralkyl—CO$_2$—Q, wherein Q is lower alkyl or —H, acyl such as acetyl, propionyl or butyryl.

A compound of formula (I) may be used as an intermediate for a corresponding compound wherein the 4-position hydrogen of the pyrazole is replaced by bromo or chloro. This is accomplished by, for example, treatment of a formula (I) compound where RCOOH is CH$_2$CH$_2$COOH with N-bromosuccinimide or N-chlorosuccinimide in a mixture of carbon tetrachloride and chloroform to afford the 4-bromo or 4-chloro derivative, respectively.

To prepare dione acids of the formula (III), one may employ the following Scheme A or Scheme B, where R, R$_1$, R$_2$, R$_3$, R$_4$ and R$_5$ are as defined above:

Scheme A:

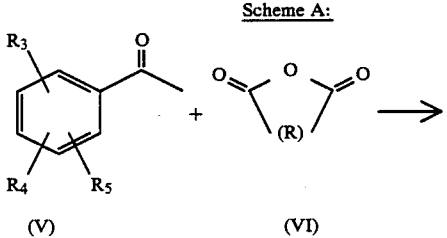

(V)          (VI)

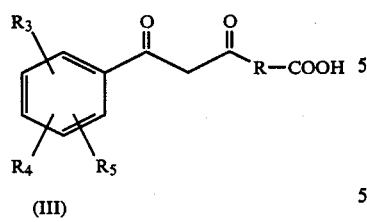

(III)

Scheme B:

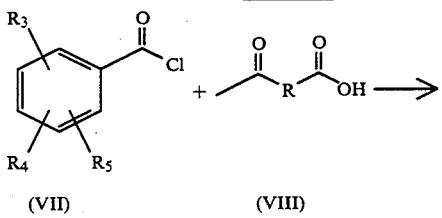

(VII)          (VIII)

-continued
Scheme B:

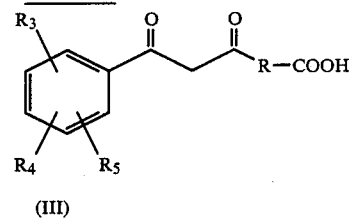

(III)

In Scheme A, an acetophenone of formula (V) is reacted with a strong base such as an alkyl lithium compound such as lithium diisopropylamide or lithium hexamethyldisilazide at a temperature of about −78° to −20° C., e.g. about −78° C. to form the corresponding lithium adduct, i.e., where the —C(O)CH$_3$ of (V) is replaced by —C(OLi)=CH$_2$. To the adduct is added the appropriate anhydride (VI), or a diacid equivalent, in a ratio of (V):(VI) of about 2.5:1. The mixture is allowed to react at about −78° to +25° C., e.g. about −78° C. and the dione acid (III) is recovered by conventional techniques.

Scheme B is used primarily to obtain dione acids of formula (III) where at least one of R$_3$, R$_4$ and R$_5$ is an electron donating substituent. In Scheme B, an acid chloride (VII) is reacted with a ketoacid (VIII), e.g. in a molar ratio of about 1.25:5. The ketoacid (VIII) is preferably activated by reaction with an alkyl lithium compound such as lithium diisopropylamide. The reaction is conducted at about −78° to −60° C., e.g. about −78° C. for about 1 hour with stirring at room temperature for about 1 day thereafter. The acid of formula (III) is then recovered by techniques known in the art.

Also part of the present invention are the dione acids of formula (III) and the process of Scheme A.

In the following Examples and throughout the specification, the following abbreviations may be used: Me (methyl); Et (ethyl); Pro (propyl); Et$_2$O (diethyl ether); Hex (hexane); Pet (petroleum ether); Ace (acetone); MeOH (methanol); DMF (dimethylformamide); ml (milliliters); g (grams); min (minutes); rt (room temperature); EtOAc (ethyl acetate); THF (tetrahydrofuran); M (molar). Unless otherwise indicated, all temperatures are reported in degrees Centigrade (°C.).

Procedure A—Synthesis of Acid (III)

Dione acids of formula (III) were synthesized by the following general procedure. To a reaction vessel containing anhydrous THF (250 ml) and diisopropylamine (14 ml, 0.1 Mole) stirring under nitrogen at 0° C. was added by syringe, n-BuLi (1.6M, 62.5 ml, 0.1 Mole). The vessel was then cooled to −78° C. Alternatively, lithium hexamethyldisilazide (0.1 Mole) may be employed as the base in place of lithium diisopropylamide. The appropriately substituted acetophenone (0.1 Mole) of formula (V), where the R$_3$, R$_4$ and R$_5$ substitutions are as in the dione acid product of formula (III), in anhydrous THF (50 ml) was added and the resulting solution was allowed to stir for 30 min at −78° C. after which succinic anhydride (4.0 g, 0.04 mole) in THF (100 ml) was added via syringe. The solution was allowed to stir for 1 hour at −78° C., warmed to rt for 1 hr and poured into 5% HCl (250 ml). The mixture was extracted with Et$_2$O (2×300 ml) and the combined ether extract was extracted with 10% NaOH (100 ml). The NaOH layer was separated and acidified with 4N HCl, and reextracted with Et$_2$O (2×300 ml). The combined ether layers were dried (Na$_2$SO$_4$), filtered and concentrated in vacuo. The resultant residues were recrystallized to give the dione acids of Table A.

In Table A, all compounds analyzed (elemental) correctly within ±0.4%.

TABLE A

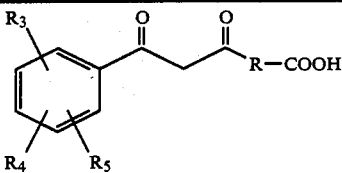

(III)

| Example | R$_3$R$_4$R$_5$ | Melting Point | Mass Spectrum (m/e, M$^+$) | Crystallization Solvent (see below) |
|---|---|---|---|---|
| ...R = —CH$_2$CH$_2$... | | | | |
| 1 | 4-Me | 139–141 | 234 | Ace/Hex |
| 2 | 3-Me | 92–94 | 234 | Et$_2$O/Pet |
| 3 | 3,4-diMe | 98–100 | 248 | Et$_2$O |
| 4 | 2-Me | 139–140 | 234 | Et$_2$O/Pet |
| 5 | 4-Et | 114–115 | 248 | Et$_2$O/Pet |
| 6 | 4-Cl | 137–139 | 254 | Et$_2$O |
| 7 | 4-F | 120–122 | 238 | Et$_2$O |
| 8 | 3,4-diCl | 87–90 | 288 | Et$_2$O/Hex |
| 9 | — | 102–105 | 220 | MeOH |
| 10 | 4-phenyl (sodium salt) | 183–186 | — | — |
| ...R = —CH$_2$CH$_2$CH$_2$... | | | | |
| 11 | 4-Cl | 127–129 | 268 | Et$_2$O |
| ...R = —CH=CH... | | | | |
| 12 | 4-Cl | 172–174 | 252 | — |

Procedure B—Synthesis of Acid (III)

Dione acids of formula (III) were also prepared according to the following alternate general procedure. To a reaction vessel containing 500 ml of dry THF and diisopropyl amine (14 ml, 0.1 moles) mechanically stirring under nitrogen at 0° C. was added by syringe n-butyl lithium 1.6M (62.5 ml, 0.1 moles). The vessel was then cooled to −78° C. 5-oxohexanoic acid of formula (VIII) where R=—(CH$_2$)$_3$ (6.5 g, 0.05 moles) in 50 ml of THF was added. The mixture began to cloud and eventually a thick slurry formed. After 15 min of stirring, anisoyl chloride of formula (VII) where R$_3$=4—OMe, R$_4$ and R$_5$=H (2.1 g, 0.0125 moles) in 50 ml THF was added. The slurry (yellow) was stirred for 1 hr at −78° C. and 24 hr at rt. The slurry was then poured into 500 ml of 10% HCl with vigorous stirring. The mixture was then extracted with 2, 300 ml portions of Et$_2$O. The combined ether fractions were dried over sodium sulfate, filtered and concentrated to a yellow oil. The oil was flash chromatographed on silica gel Hexane/EtOAc 20% to EtOAc. The pure product (725 mg) was isolated as a yellow powder. In a similar reaction, 0.05 moles of 4-oxopentanoic acid may be substituted for the 5-oxohexanoic acid to yield the product of formula (III) where R$_3$, R$_4$ and R$_5$=H and R=—(CH$_2$)$_2$—. Data for these two products are shown below in Table B wherein all compounds analyzed (elemental) correctly to within ±0.4%.

TABLE B

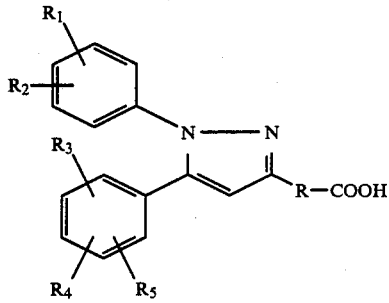

(III)

| ...R$_3$ & R$_4$ = H, R$_5$ = 4-OCH$_3$... | | |
|---|---|---|
| Example | R | Melting Point |
| 13 | —(CH$_2$)$_3$— | 113–115 |
| 14 | —(CH$_2$)$_2$— | — |

Procedure C—Synthesis of Pyrazole (I)

The following general procedure was used for the preparation of the 1,5-diaryl-3-pyrazole propionic acids of Formula (I). A mixture of the appropriate 6-aryl-4,6-diketohexonic acid (0.1 Mole) from Tables A and B or prepared by the method of Procedures A or B in methanol (750 ml) containing Et$_3$N (0.2 Mole) was treated with 4-methoxyphenylhydrazine hydrochloride (17.4 g, 0.1 Mole) at rt for 1 hr. If the reaction was incomplete at this point, it was refluxed until complete. The resulting darkened solution was evaporated in vacuo and taken up in Et$_2$O (700 ml); the ether solution was washed with aqueous 1N HCl (350 ml), brine, dried (Na$_2$SO$_4$), decolorized, evaporated in vacuo and recrystallized from Et$_2$O. The products are set forth in Table C below.

TABLE C (I)

| ...R$_1$ = 4-OCH$_3$, R = —CH$_2$CH$_2$—, R$_2$ = H... | | | |
|---|---|---|---|
| Example | R$_3$R$_4$R$_5$ | Melting Point | Mass Spectrum (m/e, M$^+$) |
| 15 | 4-Me | 145–147 | 336 |
| 16 | 3-Me | 109–110 | 336 |
| 17 | 3,4-di-Me | 141–142 | 350 |
| 18 | 2,4,6-tri-Me | 141–142 | 364 |
| 19 | 2-Me | 111–112 | 336 |
| 20 | 4-Et | 137–138 | 350 |

For the compounds of Table C, all were analyzed (elemental) to yield values ±0.4% of calculated.

Procedure D—Refunctionalization of Pyrazole (I)

EXAMPLE 21

3-[5-(4-Chlorophenyl)-1-(4-methoxyphenyl)-3-pyrazolyl]-N-hydroxy-N-methylpropanamide To a solution of the pyrazole acid of formula (I) where R$_1$, R$_3$ and R$_4$ are hydrogen; R$_2$ is 4-OCH$_3$; R$_5$ is 4-Cl; and R is —(CH$_2$)$_2$— (0.99 g, 2.77 mM) in tetrahydrofuran (THF) (20 ml) at 0° C., was added one drop of DMF and oxalyl chloride (0.29 ml, 33 mM). After 0.5 hr the cooling bath was removed and stirring was continued for an additional 0.5 hr. The reaction mixture was concentrated in vacuo to remove any excess oxalyl chloride, and the acid chloride product was taken up into THF (10 ml).

To a solution of methylhydroxylamine hydrochloride (0.35 g, 4.16 mM) and triethylamine ($Et_3N$) (1.55 ml, 11.10 mM) in THF, $H_2O$ (10 ml: 5 ml) at 0° C., was added the THF solution of the acid chloride dropwise over a 5 min period. The cooling bath was removed, and the reaction mixture was stirred for 1 hr, diluted to 100 ml with EtOAc, washed with $H_2O$, dried ($MgSO_4$), filtered, and concentrated in vacuo. Chromatography (Baker silica gel, 45 g) of the residue with EtOAc as eluent, followed by crystallization from $Et_2O$ afforded pure title product (0.70 g, 65%), mp=113°–115° C. Further recrystallization from EtOAc afforded a white crytallite solid, mp 125°–26° C.

Analysis Calculated for $C_{20}H_{20}ClN_3O_3$: C, 62.25; H, 5.22; N, 10.89; Found: C, 62.60; H, 5.18; N, 10.82.

What is claimed is:

1. A process for the preparation of 3-[5-(4-chlorophenyl)-1-(4-methoxyphenyl)-3-pyrazolyl]-N-hydroxy-N-methylpropanamide of the following formula (IX):

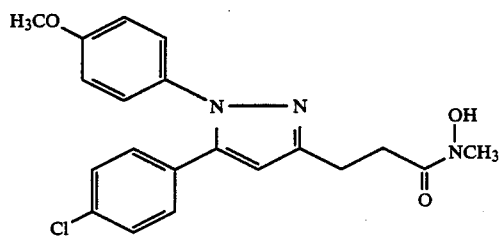

which comprises the steps of
(i) reacting a hydrazine of the following formula (X) with a diketoacid of the following formula (XI):

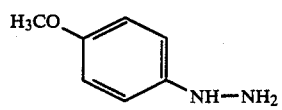

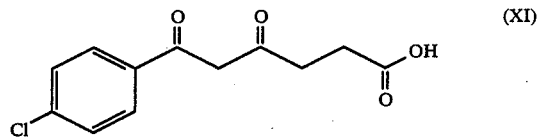

at a temperature of about 0°–100° C., to form a pyrazole acid of the following (XII):

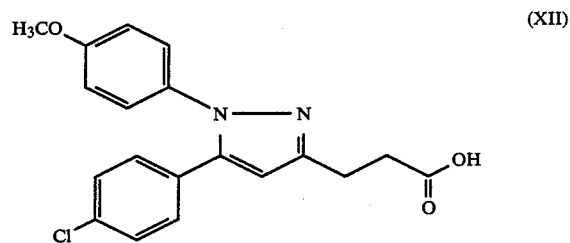

followed by
(ii) chlorinating the pyrazole acid (XII) oxalyl chloride to yield the pyrazole acid chloride of the following formula (XIII):

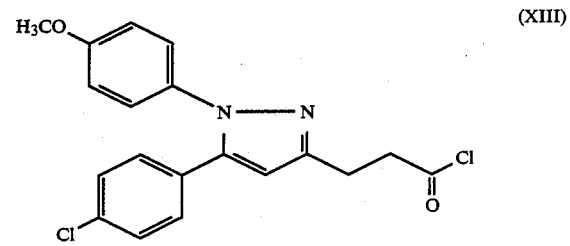

followed by
(iii) reacting the pyrazole acid chloride (XIII) with methylhydroxylamine hydrochloride to yield the methylpropanamide of formula (IX).

* * * * *

UNITED STATES PATENT AND TRADEMARK OFFICE
CERTIFICATE OF CORRECTION

PATENT NO. : 4,898,952
DATED     : Feb. 6, 1990
INVENTOR(S) : Murray et al.

It is certified that error appears in the above-identified patent and that said Letters Patent is hereby corrected as shown below:

Claim 1, Column 10, Line 28

"(XII) oxalyl"

Should be:

"(XII) with oxalyl"

Signed and Sealed this

Fourth Day of June, 1991

*Attest:*

HARRY F. MANBECK, JR.

*Attesting Officer*     *Commissioner of Patents and Trademarks*